(12) United States Patent
Endo et al.

(10) Patent No.: US 10,918,262 B2
(45) Date of Patent: Feb. 16, 2021

(54) INSERT MOLDED PRODUCT, ELECTRICAL SIGNAL CONNECTOR, ENDOSCOPE, AND INSERT MOLDING METHOD

(71) Applicant: OLYMPUS CORPORATION, Hachioji (JP)

(72) Inventors: Tetsuya Endo, Tokyo (JP); Naohito Shiga, Tokyo (JP); Kohei Shiramizu, Kawasaki (JP); Junko Nakamoto, Osaka (JP)

(73) Assignee: OLYMPUS CORPORATION, Tokyo (JP)

( * ) Notice: Subject to any disclaimer, the term of this patent is extended or adjusted under 35 U.S.C. 154(b) by 232 days.

(21) Appl. No.: 16/050,076

(22) Filed: Jul. 31, 2018

(65) Prior Publication Data

US 2018/0338671 A1 Nov. 29, 2018

Related U.S. Application Data

(63) Continuation of application No. PCT/JP2017/008323, filed on Mar. 2, 2017.

(30) Foreign Application Priority Data

Mar. 8, 2016 (JP) ................................ 2016-044827

(51) Int. Cl.
*A61B 1/00* (2006.01)
*B32B 15/08* (2006.01)
(Continued)

(52) U.S. Cl.
CPC ........ *A61B 1/00124* (2013.01); *A61B 1/0011* (2013.01); *A61B 1/00078* (2013.01);
(Continued)

(58) Field of Classification Search
CPC ... B32B 15/098; B32B 15/08; B29C 45/1418; B29C 45/14; B29C 45/14811; A61B 1/00124; H01R 13/03; H01R 13/5216
See application file for complete search history.

(56) References Cited

U.S. PATENT DOCUMENTS 3,088,847 A * 5/1963 Pines ....................... B05D 7/16
428/336
4,753,856 A * 6/1988 Haluska ................ H01L 21/314
428/698

(Continued)

FOREIGN PATENT DOCUMENTS

EP 2543636 A1 * 1/2013 ............. C01B 37/02
EP 2656779 A1 10/2013
(Continued)

OTHER PUBLICATIONS

Ishio—JP 2003-103562 A—MT—silane treatment of metal surface for bonding—2003 (Year: 2003).*
(Continued)

*Primary Examiner* — Callie E Shosho
*Assistant Examiner* — John Vincent Lawler
(74) *Attorney, Agent, or Firm* — Holtz, Holtz & Volek PC

(57) ABSTRACT

An insert molded product in which a metal base member and a resin are bonded together includes a ground layer; a noble metal layer formed of a noble metal; a compound layer formed of a compound containing silicon (Si) and oxygen (O); and a mixture layer where the compound and the resin are mixed together, wherein the ground layer, the noble metal layer, the compound layer, and the mixture layer are formed in this order on the metal base member, and wherein nickel (Ni) is included in both the compound layer and the mixture layer.

15 Claims, 4 Drawing Sheets

(51) Int. Cl.
| | |
|---|---|
| *H01R 13/405* | (2006.01) |
| *B29C 45/14* | (2006.01) |
| *A61L 29/10* | (2006.01) |
| *A61B 18/14* | (2006.01) |
| *A61L 29/02* | (2006.01) |
| *A61L 29/06* | (2006.01) |
| *C08J 5/18* | (2006.01) |
| *H01R 13/03* | (2006.01) |
| *H01R 13/52* | (2006.01) |
| *B29K 705/00* | (2006.01) |
| *A61B 18/00* | (2006.01) |
| *B29K 71/00* | (2006.01) |
| *B29K 705/14* | (2006.01) |
| *B29L 31/00* | (2006.01) |
| *B32B 1/00* | (2006.01) |

(52) U.S. Cl.
CPC ...... *A61B 1/00128* (2013.01); *A61B 18/1482* (2013.01); *A61L 29/02* (2013.01); *A61L 29/06* (2013.01); *A61L 29/106* (2013.01); *B29C 45/14* (2013.01); *B29C 45/14811* (2013.01); *B32B 15/08* (2013.01); *C08J 5/18* (2013.01); *H01R 13/03* (2013.01); *H01R 13/405* (2013.01); *H01R 13/521* (2013.01); *H01R 13/5216* (2013.01); *A61B 2018/00148* (2013.01); *A61B 2018/00178* (2013.01); *A61B 2018/00601* (2013.01); *A61L 2420/06* (2013.01); *A61L 2420/08* (2013.01); *B29C 2045/14868* (2013.01); *B29K 2071/00* (2013.01); *B29K 2705/00* (2013.01); *B29K 2705/14* (2013.01); *B29L 2031/7546* (2013.01); *B32B 1/00* (2013.01); *B32B 2535/00* (2013.01); *C08J 2371/10* (2013.01); *H01R 13/5224* (2013.01); *H01R 2201/12* (2013.01)

(56) References Cited

U.S. PATENT DOCUMENTS

| | | | | |
|---|---|---|---|---|
| 5,097,317 | A | * | 3/1992 | Fujimoto ................. C08K 3/08 |
| | | | | 257/786 |
| 2005/0019580 | A1 | * | 1/2005 | Yasuhiro ................. B29C 59/08 |
| | | | | 428/409 |
| 2009/0148634 | A1 | | 6/2009 | Fuertsch et al. |
| 2011/0287225 | A1 | | 11/2011 | Decarmine |
| 2013/0197309 | A1 | | 8/2013 | Sakata |
| 2015/0109722 | A1 | * | 4/2015 | Toyota .............. B29C 45/14639 |
| | | | | 361/679.01 |
| 2017/0028684 | A1 | * | 2/2017 | Imai .................... B29C 45/1418 |

FOREIGN PATENT DOCUMENTS

| | | | | | |
|---|---|---|---|---|---|
| JP | H08213070 | A | | 8/1996 | |
| JP | 2003/103562 | | * | 4/2003 | ............ B29C 45/14 |
| JP | 2007173224 | A | | 7/2007 | |
| JP | 2007/296769 | | * | 11/2007 | ............ B29C 45/14 |
| JP | 2007296769 | A | | 11/2007 | |
| JP | 2009520610 | A | | 5/2009 | |
| JP | 2012516022 | A | | 7/2012 | |
| JP | 2012157991 | A | | 8/2012 | |
| JP | 2013118174 | A | | 6/2013 | |
| JP | 2014/185345 | | * | 9/2014 | ........... B32B 15/098 |
| JP | 5945650 | B1 | | 7/2016 | |
| WO | 2010085419 | A1 | | 7/2010 | |
| WO | 2013114703 | A1 | | 8/2013 | |

OTHER PUBLICATIONS

Iizuki—JP 2007-296769 A—ISR D#3—MT—insert molding—2007 (Year: 2007).*
International Search Report (ISR) dated Apr. 25, 2017 issued in International Application No. PCT/JP2017/008323.
Written Opinion dated Apr. 25, 2017 issued in International Application No. PCT/JP2017/008323.

* cited by examiner

INSERT MOLDED PRODUCT, ELECTRICAL SIGNAL CONNECTOR, ENDOSCOPE, AND INSERT MOLDING METHOD

This application is a continuation application based on a PCT International Application No. PCT/JP2017/008323, filed on Mar. 2, 2017, whose priority is claimed on a Japanese Patent Application No. 2016-044827, filed on Mar. 8, 2016. The contents of both the PCT International Application and the Japanese Patent Application are incorporated herein by reference.

BACKGROUND OF THE INVENTION

Field of the Invention

The present invention relates to an insert molded product, an electrical signal connector including the insert molded product, an endoscope including the insert molded product, and an insert molding method.

Description of Related Art

An insert molding method is a method of manufacturing a molded product by injecting a resin material around a metal core member. Among the conventional insert molded products, bonding of the core member and the resin can only be realized by close contact between the core member and the resin, or a shrinkage pressure due to the molded resin. Accordingly, a bonding force between the core member and the resin material is insufficient such that it is difficult to achieve a molded product with watertight characteristics.

For example, in Published Japanese Translation No. 2009-520610 of the PCT International Publication, an injection molded member having a metal anticorrosion protective layer at least on an outside surface of the core member is disclosed. In the injection molded member of Published Japanese Translation No. 2009-520610 of the PCT International Publication, a sealing layer is extracted from the anticorrosion protective layer and the resin is injected around outside of the sealing layer. In Japanese Unexamined Patent Application, First Publication No. 2012-157991, a metal-resin composite manufactured by forming a chemical conversion treatment layer on a surface of an aluminum-silicon alloy and injecting a resin composite containing polyphenylene sulfide or polybutylene terephthalate as a main component to the surface is disclosed.

SUMMARY OF THE INVENTION

According to a first aspect of the present invention, an insert molded product in which a metal base member and a resin are bonded together includes a ground layer, a noble metal layer formed of a noble metal, a compound layer formed of a compound containing silicon (Si) and oxygen (O), and a mixture layer where the compound and the resin are mixed together formed in this order on the metal base member, and wherein nickel (Ni) is included in both the compound layer and the mixture layer.

According to a second aspect of the present invention, in the insert molded product according to the first aspect, the ground layer may be a nickel layer.

According to a third aspect of the present invention, in the insert molded product according to the first or the second aspect, the nickel in the compound layer and the mixture layer may be a nickel compound.

According to a fourth aspect of the present invention, in the insert molded product according to the third aspect, the nickel compound may be a compound including the nickel (Ni) and the oxygen (O).

According to a fifth aspect of the present invention, in the insert molded product according to the third aspect, the nickel compound may be a silicate containing the nickel.

According to a sixth aspect of the present invention, in the insert molded product according to the first to the fifth aspect, the resin may be a polyether ether ketone resin (PEEK).

According to a seventh aspect of the present invention, in the insert molded product according to the first to the sixth aspect, the noble metal may be gold.

According to an eighth aspect of the present invention, in the insert molded product according to the first to the seventh aspect, a thickness of the compound layer containing the silicon and the Oxygen may be between 1 nanometer to 10 micrometers inclusive.

According to a ninth aspect of the present invention, in the insert molded product according to the first to the eighth aspect, the metal base member may be a cylindrical electrical signal terminal.

According to a tenth aspect of the present invention, an electrical signal connector includes the insert molded product according to the first to the eighth aspect.

According to an eleventh aspect of the present invention, an endoscope includes the insert molded product according to the first to the ninth aspect.

According to a twelfth aspect of the present invention, an insert molding method for bonding a metal base member and a resin includes a process of forming a ground layer on a surface of the metal base member, a process of forming a noble metal layer with a thickness equal to or less than 0.5 micrometers on a surface of the ground layer, a process of forming a layer of a compound containing silicon (Si) and oxygen (O) with a thickness equal to or less than 10 micrometers on a surface of the noble metal layer, and a process of introducing the resin with a temperature equal to or more than 200 degree Celsius by insert molding so that the introduced resin is in contact with the layer of the compound.

According to a thirteen aspect of the present invention, in the insert molding method according to the twelfth aspect, the layer of the compound containing the silicon (Si) and the oxygen (O) may be formed of a chemical vapor deposition method (CVD).

According to a fourteenth aspect of the present invention, in the insert molding method according to the twelfth or the thirteenth aspect, the ground layer may be formed as a nickel (Ni) layer.

DETAILED DESCRIPTION OF THE INVENTION

An embodiment of the present invention will be described. An insert molded product according to the embodiment of the present invention is formed of bonding a metal base member and a resin. In the insert molded product and between the metal base member and the resin, a nickel (Ni) layer, a noble metal layer, a compound layer formed of a compound containing silicon (Si) and oxygen (O) (hereinafter described as "compound layer"), and a mixture layer where the compound of the silicon and oxygen and the resin are mixed together are formed in this order on the metal base member. The nickel (Ni) exists in the compound layer and the mixture layer of the insert molded product. A typical example of the insert molded product is a metal-resin composition material.

The compound refers to a material formed of any of covalent bonding, coordinate bonding, ionic bonding, metallic bonding, hydrogen bonding, and van der Waals bonding.

Figure 1:
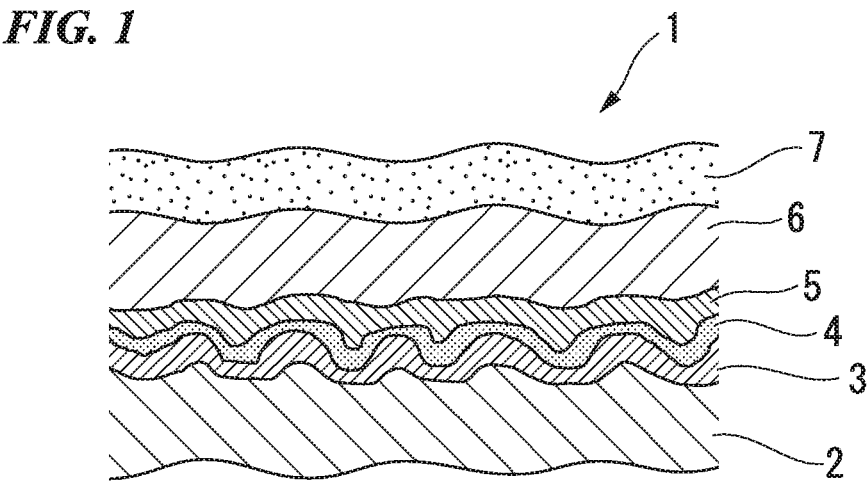
FIG. 1 is a schematic view showing a layer composition of an insert molded product according to an embodiment of the present invention.

FIG. 1 is a schematic view showing a cross section of a layer composition of a boundary portion between a metal base member 2 and a resin portion 7 of an insert molded product 1 according to the present embodiment. The insert molded product 1 includes a nickel (Ni) layer 3 (ground layer), a noble metal layer 4, a compound layer 5 formed of a compound including silicon (Si) and oxygen (O), a mixture layer 6 where the materials forming the compound layer 5 and the resin forming the resin portion 7 are mixed together, and the resin portion 7, wherein the layers are formed in this order on a surface of the metal base member 2.

It is considered that the nickel existed in the compound layer 5 and the mixture layer 6 forms a Ni—O—Si bond via Si and O. Such an insert molded product is manufactured by using the metal base member 2, on which the Ni layer 3 as the ground layer of the noble metal layer 4 is formed in advance, as a core member of the insert molding, forming the compound layer 5 from the compound containing Si and O on the noble metal layer 4, and injecting the resin forming the resin portion 7 to form the mixture layer 6 in which the materials forming the compound layer 5 and the resin forming the resin portion 7 are mixed together.

A material of the metal base member 2 is formed of materials selected from the group consisting of copper (Cu), ferrum (Fe), manganese (Mn), zinc (Zn), stannum (Sn), cobalt (Co), magnesium (Mg), zirconium (Zr), aluminum (Al), chromium (Cr), and titanium (Ti). Any one material selected from the group may be independently used, or two or more than two materials may be mixed together and used. The metal base member 2 may be formed in any suitable shape in accordance with the desired insert molded product.

A preferable material of the metal base member 2 is the copper (Cu). An electric resistance value and cost of Cu is low such that Cu is suitably used in the components relating to electrical signals such as the electrical signal terminals.

The Ni layer 3 is formed on the metal base member 2 by metallizing plating. Ni has superior corrosion resistance characteristic, fine physical characteristic such as hardness, flexibility and the like, and fine color that discoloration is difficult to occur. Furthermore, adhesion between Ni and the metal base member 2 as the ground is good such that the adhesion between Ni and the noble metal layer 4 is also good. In a situation in which Cu is used as the metal base member 2 due to a high level diffusion ability in other metal, there are merits of suppressing the diffusion of Cu as the material of the metal base member 2 in the Ni layer. In addition to Ni, the material such as Zn, Mg, and Zr which has an ionic radius equal to or less than that of Ni such that diffusion in the noble metal is easy to occur can be used as the material for forming the ground layer. Any one material may be independently used, and two or more than two materials may be mixed together and used.

The noble metal layer 4 is formed on the Ni layer 3 by metallizing plating. The noble metal forming the noble metal layer 4 can be selected from gold (Au), silver (Ag), platinum (Pt), palladium (Pd), rhodium (Rd), and rubidium (Ru). Any one material may be independently used, and two or more than two materials may be mixed together and used. It is preferable that the noble metal layer 4 has a thickness equal to or less than 0.5 micrometers in order to fully exhibit the diffusion effect of Ni which will be described later.

A preferable material for forming a conductive thin film as the noble metal layer 4 is Au. Au is suitably used in the components relating to electrical signals such as the electrical signal terminals due to its high transmission efficiency. Also, Au has high endurance such that it is difficult to rust. Furthermore, Au has a high chemical resistance characteristic. Conventionally, even if some processing layer is formed on a surface of inactive metal such as Au during the metallizing plating, an exfoliation of the inactive metal is still easy to occur such that gold-plating is not used in the components necessary to have watertight characteristic. However, in the present invention, since the compound layer 5 including Si and O is formed on the gold-plating as the noble metal layer 4 and the resin portion 7 is then formed on the compound layer 5 by injection molding, decrease of the adhesion between the noble metal layer 4 (gold-plating) and the compound layer 5 does not occur and the watertight characteristic is maintained at a high level such that the gold-plating is possible to carry out.

Next, the compound layer 5 formed on a surface of the noble metal layer 4 will be described. The compound layer 5 is formed of a compound containing Si and O. The compound layer 5 is a layer formed of a conductive thin film. For example, such a conductive thin film can be configured by a thin film formed from a conductive material, a thin film having a conductive structure such as a porous structure and the like, and a thin film being conductive due to an extremely small thickness. The configuration of the conductive thin film is not limited thereto. However, it is preferable that the compound layer 5 is a thin film formed of a porous body, or a thin film formed of a mixture material of the porous body and an organic compound. The compound layer 5 is conductive such that the conductive characteristic of the metal base member 2 and the Ni layer 3 is not obstructed. The compound layer 5 may be formed on the whole surface of the metal base member 2 or the Ni layer 3, or the compound layer 5 may be formed on part of the surface thereof.

The compound including Si and O for composing the compound layer 5 can be adopted as silicon dioxide, silicon monoxide, and silicon hydroxide. Such materials are abundantly present in the nature and have high biocompatibility.

Accordingly, these materials are particularly suitable for forming the insert molded product used in an endoscope. Except Si, the compound for forming the compound layer 5 can be selected from the compounds of element among Ti, Al, Zr, Zn, Cr, Ni, Fe, molybdenum (Mo), boron (B), beryllium (Be), indium (In), and Sn. Any one of the compounds can be independently used, or two or more than two compounds can be mixed together and used.

A thickness of the compound layer 5 is preferably equal to or more than 1 nanometer, while be equal to or less than 10 micrometers. The thickness of the compound layer 5 is further preferably equal to or less than 1 micrometer, more preferably equal to or less than 100 nanometers. If the thickness of the compound layer 5 is too large, cohesive failure of the compound layer is easy to occur such that it may be the reason of the decrease of the watertight characteristic.

Next, the resin portion 7 will be described. The resin portion 7 is formed on at least part of the metal base member 2, or the Ni layer 3, or the noble metal layer 4, and the resin portion 7 tightly adheres to the compound layer 5. The resin portion 7 may be formed in any suitable shape in accordance with the desired insert molded product.

The resin portion 7 is preferably formed of a polymer material with high endurance. The material for forming the resin portion 7 can be adopted as thermoplastic resins that can be injection molded. Any one of the resins can be independently used, and two or more than two resins can be mixed together and used.

For example, the thermoplastic resins can be selected among the resins such as polyetherimide, liquid crystal polymer, polyphenyl sulfone, denaturated-polyphenyleneether, polyether sulphone resin, polyimide resin, polysulphone resin, polyphenylene sulfide resin, ethylene-tetrafluoroethylene copolymer, polyvinyl fluoride resin, Tetrafluoroethylene-perfluoroether copolymer, tetrafluoroethylene-hexafluoropropylene copolymer, ethylene-trifluorochloroethylene copolymer, polytetrafluoroethylene resin, polyvinylidene fluoride resin, polytrifluorochloroethylene resin, and aromatic polyketones.

The thermoplastic resin is preferably polyether ether ketone resin (PEEK). The PEEK resin has superior endurance and formability such that the PEEK resin is particularly suitable for forming the insert molded product used in the endoscope. Further, the temperature of the PEEK resin during the insert molding is high (equal to or higher than 200 degree Celsius) such that the diffusion of Ni from the Ni layer 3 to the noble metal layer 4, and the bond formation between the compound layer 5 and the Ni layer 3 (Ni—O—Si bond), for example the formation of strong silicate such as $Ni_2SiO_4$ is considered to be initiated. Accordingly, the PEEK is preferably used as the thermoplastic resin.

Next, the mixture layer 6 in which the materials forming the compound layer 5 and the materials forming the resin portion 7 are mixed together will be described. During the formation of the mixture layer 6, in order to forma stronger mixture layer 6, the compound layer 5 is preferably porous (with multiple holes). Once the compound layer 5 is porous, it is easy for the resin material to spread to the inside of the compound layer 5 during the injection molding. A preferable density of the compound layer 5 is different due to the difference of the materials. Several examples of the preferable density of different materials are shown as follows. Once the density is too low, strength of the compound layer 5 will decrease. Accordingly, densities d20 of the different materials are preferably in the ranges shown as follows, respectively.

Silicon dioxide: 1.1-2.2 $g/cm^2$
Titanium oxide: 1.9-4.3 $g/cm^2$
Aluminum oxide: 1.9-4.1 $g/cm^2$
Zirconium oxide: 2.4 $g/cm^2$
Zinc oxide: 2.8-5.6 $g/cm^2$
Chromium trioxide (Cr(III)): 2.6-5.2 $g/cm^2$
Nickel oxide: 3.3-6.7 $g/cm^2$ It is considered that the compound layer 5 and the mixture layer 6 have a bond formed of Ni and Si via O. Accordingly, in the mixture layer 6, Ni and Si have more than one valence. For example, it is considered that the covalent bonding of Ni—O—Si due to the formation of the silicate ($Ni_2SiO_4$) by hydrolysis reaction of silica, and acid-base interaction of NiO—SiO due to the formation of $Ni(OH)_2$ and NiO are contributing.

In the insert molded product 1 according to the present embodiment, the compound layer 5 exists between the noble metal layer 4 and the resin portion 7 such that it is easy for the resin of the resin portion 7 to spread to the uneven microstructure on the surface of the noble metal layer 4. As a result of anchor effect, the resin portion 7 tightly adheres to the noble metal layer 4. Accordingly, it is possible to maintain the watertight characteristic of the insert molded product 1 according to the present embodiment at a high level.

In the insert molded product 1 according to the present embodiment, comparing to the molded product manufactured by the conventional adhesion agent, the endurance characteristic such as the chemical resistance characteristic and heat resistance characteristic can be improved. Accordingly, for example, even cleaning and sterilization of an endoscope is performed of an autoclave process using acid, chemical substance, and steam with high-temperature and high-pressure, it is possible to maintain the watertight characteristic at a high level for a long time.

Furthermore, a structure of the insert molded product 1 for sealing and a sealing process during the manufacture of the insert molded product 1 using the adhesion agent as that of the conventional molded product are not necessary. Accordingly, it is possible to achieve a molded product with better quality, and the molded product can be manufactured by an easy process at low cost.

(Insert Molding Method)

A manufacture method (insert molding method) for manufacturing the insert molded product 1 according to the present embodiment will be described. The insert molding method is a method of insert molding the metal base member 2 and the resin. The insert molding method includes a process of forming the Ni layer (ground layer) 3 and subsequently the noble metal layer 4 on the surface of the metal base member 2, a process of forming the layer 5 of the compound containing Si and O (compound layer) with a thickness equal to or less than 10 micrometers on the surface of the noble metal layer 4, and a process of insert molding the resin in connection with the compound layer 5.

The method of forming the Ni layer 3 on the metal base member 2 is not specifically limited thereto, and well-known method such as electrolytic plating, electroless plating, PVD method (physical vapor deposition method), and CVD method (chemical vapor deposition method) can be adopted. By such methods, even if a thin layer can be easily formed at low cost.

The noble metal layer 4 with a thickness equal to or less than 0.5 micrometers is formed on the Ni layer 3. The thickness equal to or less than 0.5 micrometers indicates a maximum value of the thickness of the noble metal layer 4, however a value of zero (none noble metal layer) is not include therein. The method of forming the noble metal layer 4 on the Ni layer 3 is not specifically limited thereto, and well-known method such as electrolytic plating, electroless plating, PVD method, and CVD method can be adopted. By such methods, even if a thin layer can be easily formed at low cost.

Next, the compound layer 5 with a thickness equal to or less than 10 micrometers is formed on the surface of the noble metal layer 4. The thickness equal to or less than 10 micrometers indicates a maximum value of the thickness of the compound layer 5, however a value of zero (none compound layer) is not include therein. The method of forming the compound layer 5 on the surface of the noble metal layer 4 is not specifically limited thereto, and well-known method such as sputtering method, electron beam evaporation method, ion plating method, CVD method, pyrosol method, spray method, dip method and the like can be adopted. Among these methods, the CVD method is preferable and a thermal CVD method is particularly preferable. The thermal CVD method has merits that it is easy to form a thin film, and a fast film formation speed and a large processing area with respect to a scale of the film formation apparatus can be achieved.

The process of forming the compound layer 5 on the surface of the noble metal layer 4 may be performed of firstly setting the core member with the Ni layer 3 and the noble metal layer 4 formed in this order on the surface of the metal base member 2 in flames, and then spraying a solution of compound at least including element Si in the flames by thermal CVD method. For example, such a solution of compound may include at least one element selected among a group of Ti, Al, Zr, Zn, Cr, Ni, Fe, Mo, B, Be, In, and Sn.

The compound layer 5 can be formed according to another variation of the process of forming the compound layer 5 shown as follows. Firstly, a sol is formed of performing hydrolysis or polymerization with respect to a metal precursor of metal oxide. Then, the metal base member 2 with the Ni layer 3 and the noble metal layer 4 formed in advance is immersed in the sol, and in this state, an electric current is provided to the sol with the metal base member 2 as a negative pole. Subsequently, the metal base member is lifted up and heat continuously. Thus, a gel layer of the metal oxide is formed on the surface of the metal base member 2. Finally, the compound layer 5 can be formed of performing a heat treatment with respect to the gel layer to achieve a predetermined density.

An alkoxysilane compound is considered to be an example of the metal precursor of metal oxide. The alkoxysilane compound can be selected from ethoxide, methoxide, isopropoxide and the like. For example, tetraethoxysilane and tetramethoxysilane can be used. The alkoxysilane compound can be used independently and the alkoxysilane compound can be used by combining various types.

The compound layer 5 can be formed according to another variation of the process of forming the compound layer 5 shown as follows. Firstly, micelle particles are formed of dissolving surfactant in an alkali aqueous solution with a concentration equal to or above a critical micellar concentration. Then, the solution is left until micelle particles take a filling structure and colloidal crystals are formed. Subsequently, silica sources such as the tetraethoxysilane and the like, are added into the solution, and a minute amount of acid or bases is also added into the solution as catalyst. Accordingly, a sol-gel reaction is proceeded in the gaps among the colloidal particles to form a silica gel skeleton. Then, the solution is coated on the metal base member 2 with the Ni layer 3 and the noble metal layer 4 formed in advance as the ground layers, and the metal base member 2 is fired at a high temperature to degrade and remove the surfactant such that a pure mesoporous silica layer (compound layer 5) can be formed.

The surfactant can be adopted from any of cationic surfactant, anionic surfactant, nonionic surfactant, and triblock copolymer. The surfactant is preferably the cationic surfactant. The cationic surfactant is not specifically limited thereto, and quaternary ammonium salt cationic surfactants, such as octadecyl trimethyl ammonium bromide, hexadecyl trimethyl ammonium bromide, tetradecyltrimethyl ammonium bromide, dodecyl trimethyl ammonium bromide, decyl trimethyl ammonium bromide, octyl trimethyl ammonium bromide, hexyl trimethyl ammonium bromide and the like, are preferable since suitable mesoporous silica particles can be easily manufactured.

In the insert molding method according to the present invention, the metal base member 2 laminated by the Ni layer 3, the noble metal layer 4, and the compound layer 5 formed based on the above described method is inserted into a cavity of a mold and then the mold is closed. Subsequently, the mixture layer 6, in which the material of the compound layer 5 and the resin as the material of the resin portion 7 are mixed together, is formed of injecting the resin into the mold to cause the resin and the compound layer 5 to mix at a boundary thereof. At this time, the resin is injected at a temperature equal to or higher than 200 degree Celsius such that Ni diffuses from the Ni layer 3 to the compound layer 5 via the noble metal layer 4. The Ni diffused to the compound layer 5 is also included in the mixture layer 6. As a result, the bonding of Ni and Si via O in the compound layer 5 and the mixture layer 6 is promoted such that in the mixture layer 6 in which both the compound including Si and O and the resin forming the resin portion 7 are existed, the mixture layer 6 is strengthened due to the promotion of formation of silicate ($Ni_2SiO_4$) by the hydrolysis of the silica and the adhesion between the metal base member 2 and the resin portion 7 is improved.

In the above described insert molding method, in a situation when a crystalline resin is used in the resin portion 7, it is possible that the effect of the adhesion improvement between the metal base member 2 and the resin portion 7 will degrade because of a rapid cooling of the crystalline resin in the mold. However, the effect of the adhesion improvement can be maintained by taking enough time for heating the metal base member 2 to the temperature of the mold after the metal base member 2 laminated by the Ni layer 3, the noble metal layer 4, and the compound layer 5 is inserted into the cavity of the mold.

In the above described insert molding method, during the time when the resin is injected, by utilizing the pressure of the injection molding, the resin enters the gaps of the compound layer 5 to form the mixture layer 6 in which the material forming the compound layer 5 and the resin forming the resin portion 7 are mixed together. Accordingly, it is preferable that the compound layer 5 is porous since it is easy for the resin to infiltrate inside the compound layer 5 due to the pressure of the injection molding.

In the above described insert molding method, chemical reactions are promoted since the resin is injected at a high temperature equal to or more than 200 degree Celsius. That is, in the compound layer 5, the Ni—O—Si bonding due to the formation of silicate ($Ni_2SiO_4$) by the hydrolysis of the silica, the acid-base interaction of the NiO—SiO between $Ni(OH)_2$ and NiO and the like are promoted.

The insert molded product 1 according to the present embodiment has chemical resistance characteristic and heat resistance characteristic at a high level such that the insert molded product 1 is suitably used in the members for an endoscope. Also, it is easy to manufacture molded products with superior watertight characteristic and endurance by the insert molding method such that the insert molded product 1 also can be used in various products or members of apparatus. Next, examples of the insert molded product and the apparatus including the insert molded product will be described.

Figure 2:
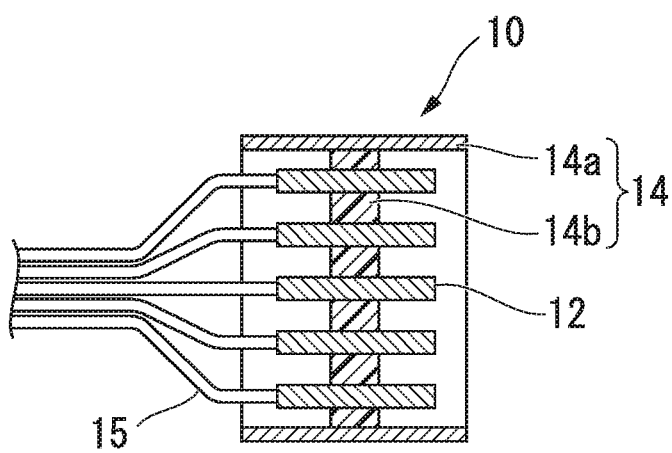
FIG. 2 is a schematic view showing a cross section of an electrical signal connector for an endoscope according to the embodiment of the present invention.

FIG. 2 is a schematic view showing a cross section of an electrical signal connector 10 including the insert molded product 1 which is used for an endoscope. The electrical signal connector 10 includes a plurality of electrical signal terminals 12, a plurality of electrical cables 15 connected to one end of the plurality of electrical signal terminals 12 respectively. The electrical signal connector 10 is configured such that the plurality of electrical signal terminals 12 are inserted into a plurality of electrical signal terminal fixing members 14b disposed inside an outer tube 14a having a tubular shape. Each of the plurality of electrical signal terminals 12 has a cylindrical shape and the insert molded product 1 according to the present embodiment. That is, each of the plurality of electrical signal terminals 12 is configured to have the metal base member 2 having a cylindrical shape and formed from Cu, wherein the metal base member 2 is laminated by the Ni layer 3 as the ground layer and the noble metal layer 4 sequentially, the Ni layer is formed of Ni plating and the noble metal layer 4 is processed by Au plating. The electrical signal terminal fixing member 14b corresponds to the resin portion 7, and the compound layer 5 and the mixture layer 6 are formed between the noble metal layer 4 and the electrical signal terminal fixing member 14b.

In this way, the ground layer 3, the noble metal layer 4, the compound layer 5, and the mixture layer 6 are existed in the electrical signal terminal 12 such that watertight characteristic between the electrical signal terminal 12 and the resin portion 14 is maintained for a long time. Thus, this configuration can be suitably used as an electrical signal connector for an endoscope. The resistance characteristic of the watertight portion relies on the resistance characteristic of the resin material rather than that of the adhesion agent such that the resistance characteristic of the watertight portion can be improved by using resin material having high resistance characteristic. Furthermore, the electrical signal connector can be manufactured by insert molding such that it is not necessary to seal electrical contacts by using the adhesion agent. Thus, cost of the member of the electrical signal connector 10 can be decreased.

Another example of the insert molded product 1 can be a lever or a dial.

Figure 3:
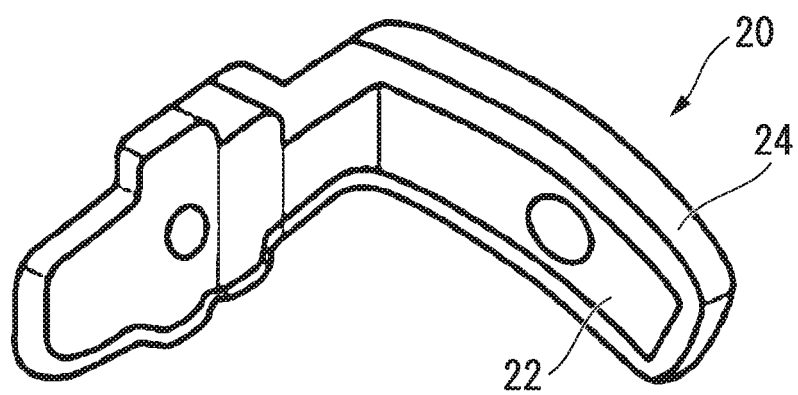
FIG. 3 is a schematic view showing a lever according to the embodiment of the present invention.

FIG. 3 is a schematic view showing a lever 20. In the lever 20, rust-resistance metal member such as stainless steel and titanium is used as a metal base member 22. The ground layer 3, the noble metal layer 4, the compound layer 5, and the mixture layer 6 are formed on a surface of the metal base member 22 (not shown), and the circumference of the lever 20 except for an internal surface is covered by a resin 24. In this way, the adhesion between the metal base member 22 and the resin 24 can be improved. Thus, in a molded product such as the lever 20 that has part of the metal base member 22 exposed, it is possible to prevent infiltration of the water and the bacterium from the boundary surface between the metal and the resin. The watertight characteristic is not easily destroyed during the cleaning process, and the disinfection and sterilization process of the endoscope such that the tight-sealing characteristic can be maintained.

Another example of the insert molded product can be a switch.

Figure 4:
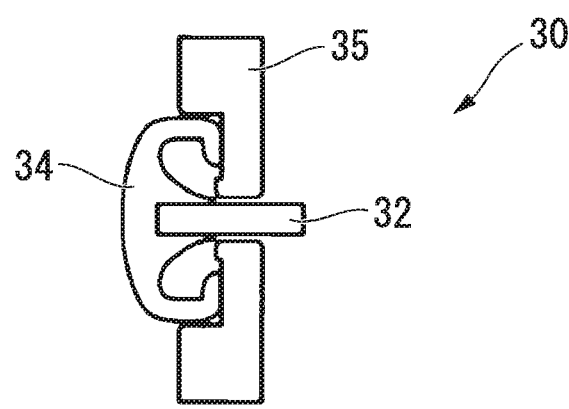
FIG. 4 is a schematic view showing a switch according to the embodiment of the present invention.

FIG. 4 is a schematic view showing a switch 30. For example, the switch 30 includes a switch actuating member 32 used as the metal base member formed from metal, and an operation member 34 formed from elastomer is attached to the switch actuating member 32 on an outer surface thereof. The switch actuating member 32 and the operation member 34 are attached to a fixing member 35.

The ground layer 3, the noble metal layer 4, the compound layer 5, and the mixture layer 6 are formed between the switch actuating member 32 and the operation member 34 (not shown). In this way, the operation member 34 formed from elastomer and the switch actuating member 32 formed from metal are firmly bonded together such that the bonding between the switch actuating member 32 and the operation member 34 is not easily destroyed even if the operation member 34 is pressed and deformed. Accordingly, it is possible to provide a member having better resistance characteristic at low cost.

Another example of the insert molded product can be an air/water supply tube system of an endoscope.

Figure 5:
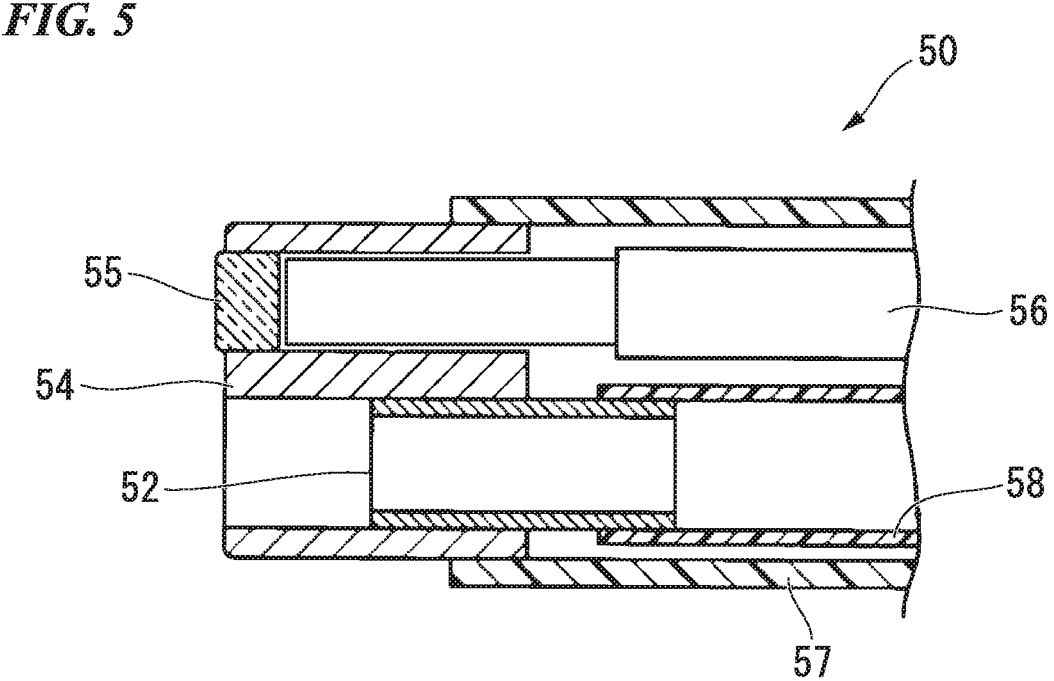
FIG. 5 is a schematic view showing a cross section of a distal end portion of the endoscope according to the embodiment of the present invention.

FIG. 5 is a schematic view showing an endoscope distal end portion 50. In the endoscope distal end portion 50, an optical transmission tube 56 and an air/water supply tube 58 are disposed inside an endoscope insertion portion 57, and the optical transmission tube 56 and the air/water supply tube 58 are connected to a distal end structural member 54 for an endoscope.

The air/water supply tube 58 formed from metal is configured to discharge or suck air, water and medicines. In the air/water supply tube 58, a tube component 52 formed from a rust-resistance metal such as stainless steel and titanium is used as the metal base member 2. One end of the tube component 52 is coupled to the distal end structural member 54, and the other end of the tube component 52 is coupled to the air/water supply tube 58. The ground layer 3, the noble metal layer 4, the compound layer 5, and the mixture layer 6 are formed on a surface of the tube component 52 (now shown). In this way, the watertight characteristic between the tube component 52 and the distal end structural member 54 or the watertight characteristic between the tube component 52 and the air/water supply tube 58 is maintained such that it is possible to prevent infiltration of the water and the bacterium from the boundary surface thereof. The watertight characteristic is not easily destroyed during the cleaning process, and the disinfection and sterilization process of the endoscope such that the tight-sealing characteristic can be maintained. As a result, it is possible to prevent the boundary surface between the members from being contaminated by the bacterium and a suitable endoscope can be provided.

In the endoscope distal end portion 50, when the water, the air, and the medicines are discharged or sucked through the water/air supply tube 58, even if a pressure difference with respect to the surrounding environment occurs, the watertight characteristic with respect to the resin on a contacting surface is maintained. Accordingly, there is no infiltration of the water and the medicines from inside to outside of the air/water supply tube 58, that is, there is no infiltration to the inside of the endoscope.

Figure 6:
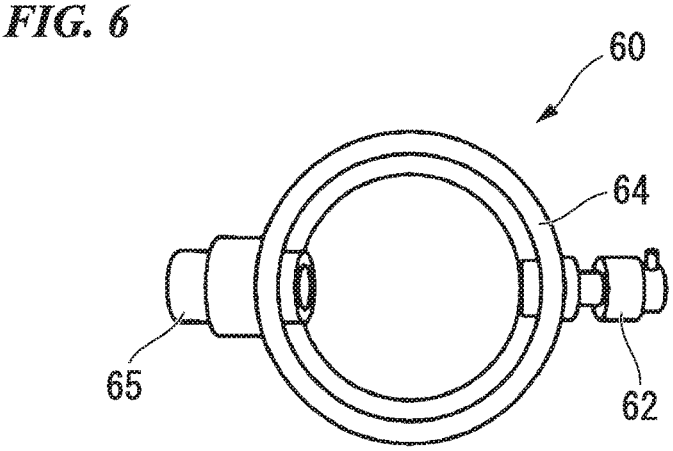
FIG. 6 is a schematic view showing a connector for connecting air supply pipes or water supply pipes according to the embodiment of the present invention.

Another example of the insert molded product 1 can be a connector connecting the air/water supply tubes and the like. FIG. 6 is a schematic view showing a connector 60 configured to connect the air/supply tubes and the like. In the connector 60, connection members 62, 65 formed from a rust-resistance metal such as stainless steel and titanium are used as the metal base member, and one end of each of the connection members 62, 65 is positioned inside a resin portion 64. The ground layer 3, the noble metal layer 4, the compound layer 5, and the mixture layer 6 are formed on surfaces of the connection members 62, 65 (not shown). In this way, the watertight characteristic at the boundary surface between the connection members 62, 65 and the resin portion 64 is maintained such that the infiltration of the water and the bacterium from the boundary surface can be prevented.

Another example of the insert molded product 1 is a watertight packing.

Figure 7:
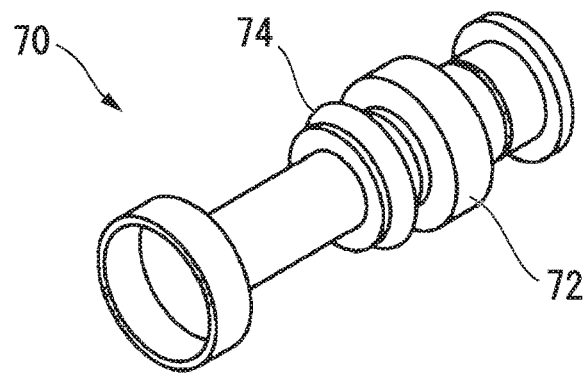
FIG. 7 is a schematic view showing a watertight packing according to the embodiment of the present invention.

FIG. 7 is a schematic view showing a watertight packing 70. In the watertight packing 70, a main body 72 formed from a rust-resistance metal such as stainless steel and titanium are used as the metal base member, and a packing 74 formed from elastomer is attached to part of the main body 72. The ground layer 3, the noble metal layer 4, the compound layer 5, and the mixture layer 6 are formed between the main body 72 and the packing 74 (not shown). In this way, the adhesion at the boundary surface between the main body 72 and the packing 74 can be achieved. Accordingly, the watertight packing 70 can secure the watertight characteristic. Furthermore, in the watertight packing 70, the resin can be insert molded directly on the rust-resistance material such that a packing having a free structure and shape in accordance with the structure and the shape of the member can be molded.

Another example of the insert molded product 1 can be an eyepiece lens cover for a rigid medical endoscope.

Figure 8:
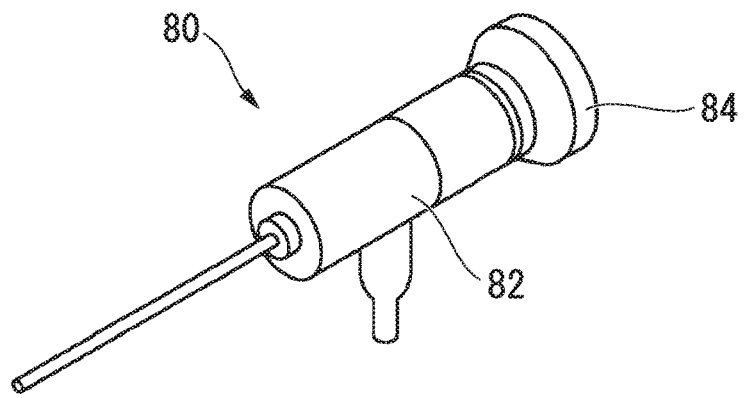
FIG. 8 is a schematic view showing a rigid endoscope according to the embodiment of the present invention.

FIG. 8 is a schematic view showing a rigid endoscope main body 80. In the rigid endoscope main body 80, a member formed from a rust-resistance metal such as stainless steel and titanium is used as a metal base member 82, and an eyepiece lens cover 84 is provided to cover the surrounding of one end of the metal base member 82. The eyepiece lens cover 84 disposed on the exterior of the metal base member 82 is configured to function as an insulator to prevent an electric current from flowing to a medical staff when an electric scalpel is used. The ground layer 3, the noble metal layer 4, the compound layer 5, and the mixture layer 6 are formed between the metal base member 82 and the eyepiece lens cover 84 (not shown). In this way, the watertight characteristic at the boundary surface between the metal base member 82 and the eyepiece lens cover 84 is maintained such that the infiltration of the water and the bacterium from the boundary surface can be prevented. The watertight characteristic is not easily destroyed during the cleaning process, and the disinfection and sterilization process of the endoscope such that the tight-sealing characteristic can be maintained.

Figure 9:
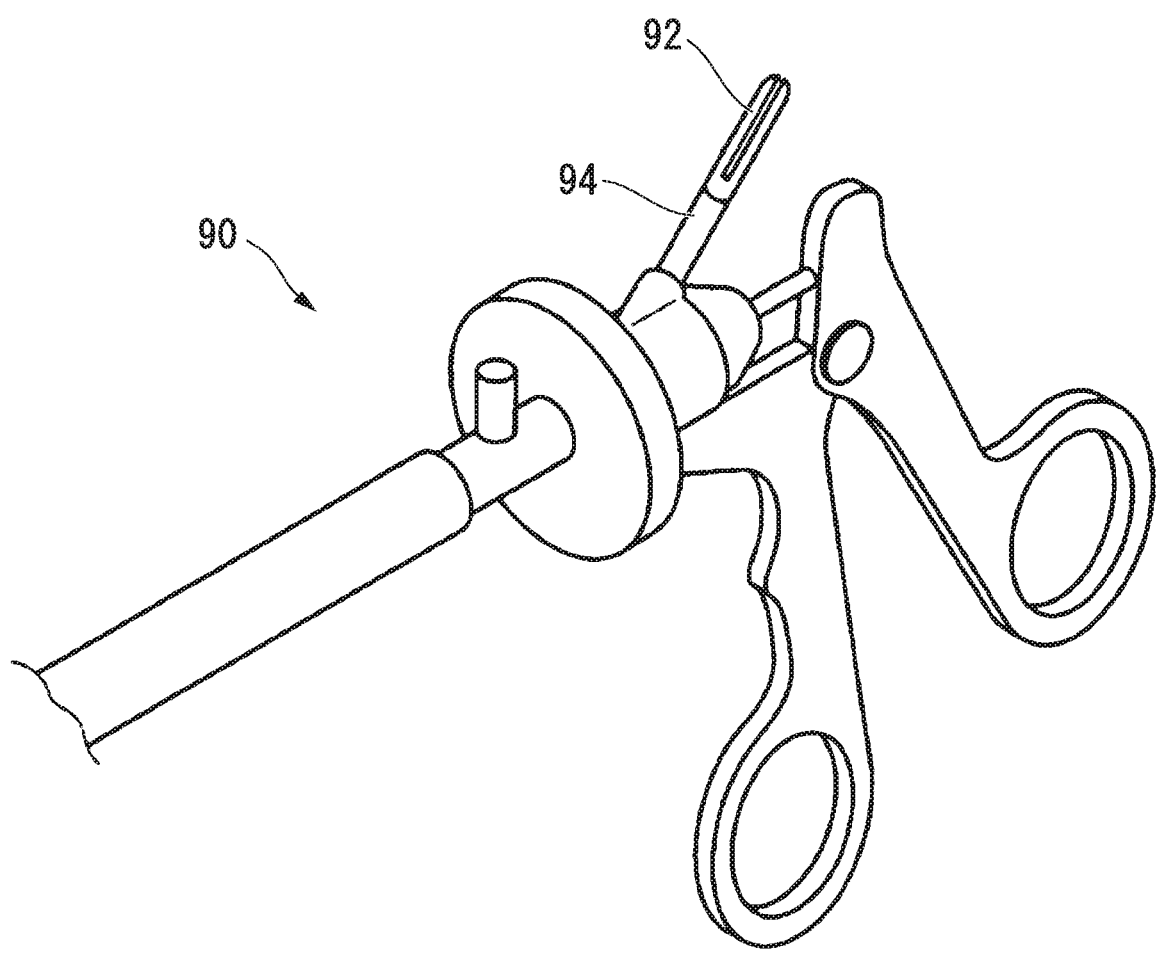
FIG. 9 is a schematic view showing a high-frequency resection apparatus according to the embodiment of the present invention.

Another example of the insert molded product can be an exterior member of a medical treatment apparatus. For example, the exterior member is a shaft, a handle and the like. An example of the treatment apparatus can be an ultrasonically activated scalpel, a high-frequency excision apparatus, an electric scalpel and the like. FIG. 9 is a schematic view showing a high-frequency excision apparatus 90. In the high-frequency excision apparatus 90, a metal member formed from a rust-resistance metal such as stainless steel and titanium is used as a metal base member 92, and the surrounding of one end of the metal base member 92 is covered by a resin portion 94. The resin portion 94 is configured to function as an insulator to prevent an electric current from flowing to a medical staff. The ground layer 3, the noble metal layer 4, the compound layer 5, and the mixture layer 6 are formed between the metal base member 92 and the resin portion 94 (not shown). In this way, watertight characteristic at the boundary between the metal base member 92 and the resin portion 94 is maintained such that the infiltration of the water and the bacterium from the boundary surface can be prevented. The watertight characteristic is not easily destroyed during the cleaning process, and the disinfection and sterilization process of the endoscope such that the tight-sealing characteristic can be maintained.

Another example of the insert molded product can be a water-proof apparatus. For example, a water-proof communication terminal such as a smartphone, a tablet and the like, or a medical communication terminal can be given as examples. With regard to electrical contacts of these terminals disposed for charging, water-proof products can be easily manufactured using the insert molded product 1 according to the present embodiment.

In these devices, a product with a conductive thin film formed on a surface of the metal such as copper, phosphor bronze and the like that has superior electrical conductivity can be used as the metal base member. For example, a plated product processed by a plating process using gold, palladium that is not only a noble metal or an inert metal but also has superior electrical conductivity, or a surface coating formed of sputter can be used as the conductive thin film.

The insert molded product 1 according to the present embodiment is applicable to an electric pot, an electric toothbrush, and a water-proof camera. Another example of the insert molded product 1 can be a gear and a shaft that are formed of forming a gear unit around a metal shaft by insert molding. It is not necessary to use adhesion agent to bond the gear and resin, and necessary strength can be achieved by the insert molding only. Accordingly, the gear and the shaft can be easily manufactured at low cost.

Another example of the insert molded product 1 according to the present embodiment can be a syringe. The syringe can be manufactured by forming the compound layer 5 on a surface of a needle used as the metal base member and forming a flange around the needle by insert molding.

In the syringe manufactured in this way, the ground layer 3, the noble metal layer 4, the compound layer 5, and the mixture layer 6 are formed between the needle and the flange (not shown) such that the watertight characteristic between the needle and the flange is maintained. The watertight characteristic between the needle and the flange can withstand pressure during the injection such that the watertight portion is not affected by various medicines and it is possible to prevent leakage of the medicines inside the syringe and contamination.

EXAMPLES

Example 1

A test piece is manufactured by forming a Ni ground layer 3 on the phosphor bronze and forming an Au plating on the ground layer 3.

The test piece is processed by spraying fuel gas including an alkyl silane compound for 0.5 seconds to form a porous silica film on a surface of the test piece. Then, the insert molding is performed of using the test piece after the surface treatment and a resin material of PEEK (manufactured by Victrex plc).

A film thickness of the formed compound layer is confirmed to be 100 nanometers using a STEM observation (Scanning Transmission Electron Microscope method).

Example 2

A test piece is manufactured by forming a Ni ground layer 3 on the phosphor bronze and forming an Au plating on the ground layer 3.

The test piece is processed by spraying fuel gas including an alkyl silane compound for 30 seconds to form a porous silica film on a surface of the test piece. Then, the insert molding is performed of using the test piece after the surface treatment and a resin material of PEEK (manufactured by Victrex plc).

A film thickness of the formed compound layer is confirmed to be 15 micrometers using the STEM observation.

Example 3

A test piece is manufactured by forming a Ni ground layer 3 on the phosphor bronze and forming an Ag plating on the ground layer 3.

The test piece is processed by spraying fuel gas including an alkyl silane compound for 0.5 seconds to form a porous silica film on a surface of the test piece. Then, the insert molding is performed of using the test piece after the surface treatment and a resin material of PEEK (manufactured by Victrex plc).

A film thickness of the formed compound layer is confirmed to be 100 nanometers using the STEM observation.

Example 4

A test piece is manufactured by forming a Ni ground layer 3 on the phosphor bronze and forming an Au plating on the ground layer 3.

The test piece is processed by spraying fuel gas including an alkyl silane compound for 0.5 seconds to form a porous silica film on a surface of the test piece. Then, the insert molding is performed of using the test piece after the surface treatment and a resin material of polyphenyl sulfone (PFSU, manufactured by Solvay).

A film thickness of the formed compound layer is confirmed to be 100 nanometers using the STEM observation.

Example 5

A test piece is manufactured by forming a Ni ground layer 3 on the phosphor bronze and forming an Au plating on the ground layer 3.

The test piece is immersed into an aqueous solution of alkali metal silicate, and then put this test piece, carbonic acid gas, and water into an airtight container to perform a carbonation treatment while keeping temperature and humidity constant. According to the treatment, a porous silica film is formed on a surface of the test piece. Then, the insert molding is performed of using the test piece after the surface treatment and the resin material of PEEK (manufactured by Victrex plc).

A film thickness of the formed compound layer is confirmed to be 10 micrometers using the STEM observation.

Comparison Example 1

A test piece is manufactured by forming a Ni ground layer 3 on the phosphor bronze and forming an Au plating on the ground layer 3.

Then, the insert molding is performed of using the test piece after the surface treatment and the resin material of PEEK (manufactured by Victrex plc).

Comparison Example 2

A test piece is manufactured by forming a Cu ground layer 3 on the phosphor bronze and forming an Au plating on the ground layer 3.

The test piece is processed by spraying fuel gas including an alkyl silane compound for 0.5 seconds to form a porous silica film on a surface of the test piece. Then, the insert molding is performed of using the test piece after the surface treatment and a resin material of PEEK (manufactured by Victrex plc).

A film thickness of the formed compound layer is confirmed to be 100 nanometers using the STEM observation.

Comparison Example 3

A test piece is manufactured by forming a Ni ground layer 3 on the phosphor bronze and forming a Cu plating on the ground layer 3.

The test piece is processed by spraying fuel gas including an alkyl silane compound for 0.5 seconds to form a porous silica film on a surface of the test piece. Then, the insert molding is performed of using the test piece after the surface treatment and a resin material of PEEK (manufactured by Victrex plc).

A film thickness of the formed compound layer including Si and O is confirmed to be 100 nanometers using the STEM observation.

<Evaluation>

The adhesion characteristic, the watertight characteristic, the sterilization resistance characteristic are evaluated using the insert molded products of the examples and the comparison examples. The adhesion characteristic is evaluated by performing a tension test using an autograph manufactured by Shimadzu Corporation to measure an adhesive force between the metal base member and the resin of the insert molded test piece. The measured strength values corresponding to the examples and the comparison examples are shown as comparative assessments with respect to the measured strength value of the example 1 while assuming the measured strength value of the example 1 is 10.

The watertight characteristic is evaluated by performing an air leakage test of putting the insert molded products corresponding to the examples and comparison examples into water and then injecting air into the insert molded products. During the air leakage test, whether air bubbles occur from the boundary surface of the test piece and the resin is observed and confirmed. In a situation when no air bubble occurs, an evaluation result is marked as "O" (good), and in a situation when the air bubbles occur, the evaluation result is marked as "X" (bad).

The sterilization resistance characteristic is evaluated by firstly using hydrogen peroxide gas to perform the sterilization with respect to the insert molded products corresponding to the examples and comparison examples for 50 times, and then performing the above described adhesion characteristic evaluation and the watertight characteristic evaluation with respect to the insert molded products after performing the sterilization for 50 times.

The evaluation results are shown in Table 1.

[Table 1]

TABLE 1

|  | before Hydrogen peroxide plasma sterilization | | after Hydrogen peroxide plasma sterilization | |
| --- | --- | --- | --- | --- |
|  | adhesion characteristic | watertight characteristic | adhesion characteristic | watertight characteristic |
| Example 1 | 10 | ○ | 10 | ○ |
| Example 2 | 7 | ○ | 7 | ○ |
| Example 3 | 10 | ○ | 9 | ○ |
| Example 4 | 10 | ○ | 7 | ○ |
| Example 5 | 7 | ○ | 7 | ○ |
| Comparison example 1 | 2 | x | 1 | x |
| Comparison example 2 | 3 | x | 2 | x |
| Comparison example 3 | 10 | ○ | 3 | x |

From Table 1, it is shown that each of the insert molded product corresponding to Example 1 to Example 5 has a high-level adhesion characteristic and watertight characteristic. Also, it is shown that after the sterilization using the hydrogen peroxide gas, the adhesion characteristic and watertight characteristic are maintained.

On the other hand, it is shown that the adhesion characteristic and watertight characteristic of the insert molded products corresponding to Comparison Example 1 and Comparison Example 2 are not enough, and the watertight characteristic of the insert molded product corresponding to Comparison Example 3 is not maintained after the sterilization.

The embodiment of the invention has been described above with reference to the drawings, but specific structures of the invention are not limited to the embodiments and may include various modifications without departing from the scope of the invention.

Also, the configuration elements of the above described embodiments and modifications can be suitably combined and configured.

What is claimed is:

1. An insert molded product in which a metal base member and a resin are bonded together, comprising:
    the metal base member;
    a ground layer;
    a noble metal layer formed of a noble metal;
    a compound layer comprising a porous silica film; and
    a mixture layer where material of the compound layer and the resin are mixed together; and
    the resin,
    wherein the ground layer, the noble metal layer, the compound layer, and the mixture layer are formed in this order on the metal base member, and
    wherein nickel (Ni) is included in both the compound layer and the mixture layer.

2. The insert molded product according to claim 1, wherein the ground layer is a Ni layer.

3. The insert molded product according to claim 1, wherein the nickel in the compound layer and the mixture layer is a nickel compound.

4. The insert molded product according to claim 3, wherein the nickel compound is a compound containing Ni and O.

5. The insert molded product according to claim 3, wherein the nickel compound is a silicate compound containing the nickel.

6. The insert molded product according to claim 1, wherein the resin is a polyether ether ketone resin (PEEK).

7. The insert molded product according to claim 1, wherein the noble metal is gold.

8. The insert molded product according to claim 1, wherein a thickness of the compound layer is between 1 nanometer to 10 micrometers inclusive.

9. The insert molded product according to claim 1, wherein the metal base member is a cylindrical electrical signal terminal.

10. An electrical signal connector comprising the insert molded product according to claim 1.

11. An endoscope comprising the insert molded product according to claim 1.

12. The insert molded product according to claim 1, wherein the ground layer is a Ni layer, and
    wherein the nickel included in both the compound layer and the mixture layer is nickel diffused from the Ni layer through the noble metal layer.

13. The insert molded product according to claim 1, wherein a thickness of the noble metal layer is not more than 0.5 micrometers.

14. An insert molding method for bonding a metal base member and a resin, comprising:
    a process of forming a ground layer on a surface of the metal base member;
    a process of forming a noble metal layer with a thickness equal to or less than 0.5 micrometers on a surface of the ground layer;
    a process of forming a layer of a compound with a thickness equal to or less than 10 micrometers on a surface of the noble metal layer, the compound containing silicon (Si) and oxygen (O) in order to form a porous silica film; and
    a process of introducing the resin with a temperature equal to or more than 200 degree Celsius by insert molding so that the introduced resin is in contact with the compound layer resulting in a mixture layer where material of the compound layer and the resin are mixed together and resulting in nickel (Ni) included in both the compound layer and the mixture layer.

15. The insert molding method according to claim 14, wherein the ground layer is a nickel (Ni) layer.

* * * * *